United States Patent [19]

Darlington

[11] Patent Number: 4,987,960
[45] Date of Patent: Jan. 29, 1991

[54] WELL FLUID AND TEST METHOD

[75] Inventor: Roy K. Darlington, Malvern, Pa.

[73] Assignee: Baroid Technology, Inc., Houston, Tex.

[21] Appl. No.: 402,051

[22] Filed: Sep. 1, 1989

[51] Int. Cl.$^5$ ........................ E21B 47/10; E21B 49/08
[52] U.S. Cl. ........................................ 175/42; 73/153; 166/250; 436/27
[58] Field of Search ...................... 175/42, 50; 166/250, 166/254; 73/153; 436/27, 30

[56] References Cited

U.S. PATENT DOCUMENTS

| | | | |
|---|---|---|---|
| 3,407,042 | 10/1968 | Slentz | 166/250 X |
| 3,563,874 | 2/1971 | Ross et al. | 423/467 X |
| 4,352,674 | 10/1982 | Fery | 166/250 X |
| 4,607,694 | 8/1986 | Sah | 166/250 |
| 4,788,848 | 12/1988 | Hsueh | 166/250 X |
| 4,807,469 | 2/1989 | Hall | 166/250 X |

*Primary Examiner*—George A. Suchfield
*Attorney, Agent, or Firm*—Browning, Bushman, Anderson & Brookhart

[57] ABSTRACT

A method of determining dilution of a well bore fluid, such as a drilling fluid, comprising preparing a drilling fluid having a known concentration of bromide ion, using the drilling fluid, recovering a sample of the used drilling fluid, determining quantitatively the concentration of bromide ion in the used drilling fluid, comparing the concentration of bromide ion in the sample drilling fluid with the known concentration of bromide ion in the drilling fluid and determining the dilution of the drilling fluid.

4 Claims, No Drawings

WELL FLUID AND TEST METHOD

BACKGROUND OF THE INVENTION

1. Field of the Invention

The present invention relates to testing of well bore fluids and, more particularly, a method of measuring changes in the well bore fluid due to dilution from connate water invasion or surface dilution.

2. Description of the Background

In well drilling, completion and workover operations, particularly well drilling operations, there is a need to know whether there has been any dilution of the well bore fluid, e.g. the drilling mud, from downhole formation water, i.e. connate water, or from surface dilution. Such dilution can change the density of the well bore fluid rendering it unsuitable for use and, in many cases, unsafe. For example, dilution of the drilling mud may lower its density to the point where it cannot maintain sufficient hydrostatic pressure in the well bore to prevent a blowout. Dilution by connate water may also be important as an indication of the nature of the formation through which the drilling is taking place. Furthermore, in workover and completion operations, it is desirable and often times necessary to know whether there has been invasion of connate water into the completion or workover fluid.

In U.S. Pat. No. 3,407,042, there is described a method of testing well samples, such as a fluid or core material, to determine whether there has been invasion of the well sample by the drilling fluid. In the method described in the patent, nitrate ion is added to the drilling mud and the concentration of nitrate ion found in the well sample compared with the concentration of that originally in the drilling mud. In the method described in the patent, the well sample is tested to determine invasion from the drilling mud. However, there is no testing of the drilling fluid per se to determine dilution by invasion either from surface fluids or connate water. Moreover, the method described in the patent utilizes a colorimetric test method which can pose difficulties when the drilling fluid contains colored additives.

SUMMARY OF THE INVENTION

It is therefore an object of the present invention to provide a method of determining the dilution of a well bore fluid by connate water or surface invasion.

Another object of the present invention is to provide a method of determining the dilution of a drilling mud which can be conducted in whole mud or mud filtrate.

Still another object of the present invention is to provide a well bore fluid which can be easily analyzed to determine dilution by connate water or surface invasion.

The above and other objects of the present invention will become apparent from the description given herein and the claims.

In one embodiment, the present invention provides a method of determining the dilution of a well bore fluid, e.g. a drilling mud, by connate water or surface invasion. In the method, a well bore fluid having a known concentration of bromide ion is prepared. The well bore fluid is then used in an earth borehole, such as in a drilling, completion or workover operation, and a sample of the thus used well bore fluid recovered. The recovered sample is analyzed to quantitatively determine the concentration of the bromide ion in the recovered sample, which is then compared with the known concentration of the bromide ion in the well bore fluid to thereby determine any dilution of the well bore fluid.

In another embodiment, the present invention provides a well bore fluid comprising water, a water-soluble source of bromide ion and a well treating agent selected from the class consisting of weighting materials, viscosifiers, fluid loss control additives and mixtures thereof.

DESCRIPTION OF THE PREFERRED EMBODIMENT

The method of the present invention is applicable to a number of well bore fluids. The term "well bore fluids," as used herein, refers to any fluid which is commonly used in drilling, completion or workover operations in the oil and gas industry. The method is especially useful with drilling fluids or muds to determine dilution from formation water, e.g. connate water, or surface dilution. The well bore fluids are those which are water based or have an aqueous phase in which can be dissolved a water-soluble source of bromide ion.

In the method of the present invention, a well bore fluid is prepared and is admixed with a suitable source of a water-soluble bromide ion, the well bore fluid being thoroughly mixed to ensure that the bromide ion source is dissolved and the bromide ion is uniformly distributed throughout the well bore fluid. It will be appreciated that insufficient mixing or distribution of the bromide ion in the drilling fluid and the well bore fluid will lead to errors in determining any dilution of the well bore fluid.

The source of bromide ion can be any water-soluble compound which will provide a source of bromide ions in the desired range. Thus, water-soluble bromide salts, such as alkali metal bromides, alkaline earth metal bromides, etc. can be employed. Generally speaking, the alkali metal bromides, such as sodium bromide, potassium bromide, etc. are preferred. The amount of water-soluble bromide added to the well bore fluid will generally be in an amount sufficient to provide a bromide ion concentration of from about 20 to about 10,000 parts per million by weight.

In order to practice the method of the present invention, it is desirable to prepare a series of calibration standards of the well bore fluid to be monitored containing various amounts of bromide ion. To this end, samples of fresh well bore fluid are admixed with varying amounts of a source of water-soluble bromide ion. These various calibration standards are then analyzed for bromide ion content and a suitable calibration curve which relates bromide ion concentration to a determinable parameter made. While other analysis techniques can be employed, the method of the present invention is particularly adapted to an electrochemical method of measuring the bromide ion concentration using a bromide ion sensitive electrode and developing a calibration curve or a plot of relative millivolts (Rel mv), the determinable parameter, versus bromide ion concentration. In developing the calibration curve, it is generally preferred to prepare, on semilog paper, a graph of millivolts versus bromide concentration. Ion sensitive electrodes are well known and widely used in analytical techniques. Such ion sensitive electrodes employ potentiometric analysis wherein direct measurement of an electrode potential from the ion sensitive electrode is directly related to the concentration of the ion under consideration. For a discussion of the method of analysis and the specific use of bromide ion sensitive electrodes, see U.S. Pat. No. 3,563,874, incorporated herein by reference. Suitable commercially available apparatus for conducting bromide ion analyses include an Orion Model 90-01 reference electrode, an Orion Model 94-35 bromide electrode and an Orion Model 901 Digital Ionalyze.

Once a suitable calibration curve has been prepared, the well bore fluid containing a known amount of bromide ion is prepared and can then be used in normal well operations, e.g., drilling, completion or workover activities. Periodically, a sample of the "spiked" well bore fluid which has been prepared can be taken and the bromide ion concentration measured. By comparing the concentration of the sampled well bore fluid with the calibration curve, the content of the bromide ion in the "used" well bore fluid can be determined, i.e. since the concentration of the bromide ion in the "spiked" well bore fluid originally prepared is known, by comparing the concentration of the bromide ion in the "used" well bore fluid with the calibration curve, it can be determined whether the bromide ion concentration has decreased from the known value thereby indicating dilution of the well bore fluid.

Compositions of well bore fluids made in accordance with the present invention are those well bore fluids which contain water, a water-soluble source of bromide ion and a well treating agent which can be a weighting material, e.g. barite, illmenite, etc., a viscosifier such as hydroxyethyl cellulose, carboxymethyl cellulose, etc. or any one of numerous fluid loss additives commonly employed in drilling, completion or workover operations. The well treating agents can be present in the well bore fluids alone or in combination depending upon the specific type of well bore fluid being formulated. The well bore fluid can also contain non-bromide ion, water-soluble salts, such as sodium chloride, calcium chloride, zinc chloride, etc. Such salts are commonly used as weighting agents, alone or in admixture with viscosifiers and fluid loss control additives, in completion and workover fluids.

To more fully demonstrate the invention, the following non-limiting examples are presented. In all cases, bromide ion measurements were made using an electrode pair of an Orion Model 90-01 Single-Junction Reference Electrode and a Model 94-35 Bromide Electrode using an Orion Model 901 Digital Ionalyzer.

EXAMPLE 1

Different amounts of dry sodium bromide were dissolved in samples of ten different well bore fluids identified as Mud G-524 and Mud G-490, so as to form mud samples containing from about 50 parts per million to about 10,000 parts per million of bromide ion on a weight basis. The samples were thoroughly stirred using a GKH-heavy duty stirrer for two minutes. Potentiometric measurements were then made on the various samples with the electrode pair with continuous stirring. Properties of Mud G-524 and Mud G-490 are listed below in Table 1. Table 2 shows a comparison of bromide ion concentration (ppm) versus Rel mv for the different samples.

TABLE 1

|  | Mud G-524 | Mud G-490 |
| --- | --- | --- |
| Initial Properties |  |  |
| Density, lb/gal | 16.3 | 12.1 |
| Color | Dark Brown | Black |
| Odor | Lignosulfonate | None |
| Settling | None | None |
| Methylene Blue Capacity, ml/ml Mud | 4.0 | 0.5 |
| Equivalent Bentonite, lb/bbl | 20.0 | 2.5 |
| Retort |  |  |
| Water, % by Volume | 68 | 83 |
| Oil, % by Volume | 0 | Trace |
| Solids, % by Volume | 32 | 18 |
| Properties After Stirring 15 Min. |  |  |
| Plastic Viscosity, cp | 60 at 80° F. | 11 at 85° F. |
| Yield Point, lb/100 sq ft | 33 | 14 |
| 10-sec gel, lb/100 sq ft | 8 | 2 |
| 10-min gel, lb/100 sq ft | 36 | 3 |
| pH | 10.4 | 9.1 |
| API Filtrate, ml | 2.8 | 13.4 |
| Anaylsis of Soluble Constituents |  |  |
| Mud Alkalinity, Pm, N50 Acid, ml | 0.90 | 1.9 |
| Calcium Sulfate, lb/bbl | 0.80 | None Listed |
| Soluble Total | 2.60 | None Listed |
| Filtrate Properties |  |  |
| Chloride, ppm | 1300 | 163,000 |
| Sulfate, ppm | 16,250 | None Listed |
| Hydroxyl, ppm | 0 | 68 |
| Carbonate, ppm | 60 | 1,320 |
| Bicarbonate, ppm | 549 | None Listed |
| Calcium, ppm | 1,000 | 40 |
| Magnesium, ppm | 0 | None Listed |

TABLE 2

| ppm of Bromide | Received Mud G-524 Rel mv | Received Mud G-490 Rel mv |
| --- | --- | --- |
| 10,000 | −134.3 | −125.5 |
| 8,000 | −129.2 | −120.4 |
| 4,000 | −113.3 | −104.7 |
| 2,000 | −95.0 | −89.6 |
| 1,000 | −77.7 | −88.2 |
| 800 | −71.8 | −85.6 |
| 400 | −56.2 | −82.3 |
| 100 | −20.1 | −72.0 |
| 50 | 3.1 | −74.5 |

Using linear regression, the following calibration equation for Mud G-524 was determined:

$$\log y = \frac{-0.01750x}{1.6379}$$

where y is the concentration of bromide ion and x if the Rel mv. The equation is found to be linear in the range from 100 ppm to 10,000 ppm of bromide ion.

The calibration curve of Mud-490 was two linear parts —one being from 2,000 ion to 10,000 ppm of bromide and the other from 100 ppm to 2,000 ppm of bromide ion. The calibration equation for 2,000 to 10,000 ppm of bromide ion is $$\log y = \frac{-0.06191x}{0.9709}$$

where x is the Rel mv and y is the concentration of bromide ion in ppm.

The calibration equation for 100 ppm to 2,000 ppm is $$\log y = \frac{-1.06919x}{0.9709}$$

where y is a bromide ion concentration in ppm and x is Rel mv. The calibration curve of Mud G-490 is thus formed to have two linear parts, i.e. from 2,000 to 10,000 ppm bromide ion and from 100 to 2,000 ppm bromide ion.

EXAMPLE 3

Mud G-490 was filtered with an API filter press to obtain a filtrate The filtrate was diluted 50% by weight with deionized water and different amounts of dry sodium bromide dissolved in the diluted filtrate to obtain samples containing from about 50 ppm to 10,000 ppm of bromide ion on a weight basis. The samples were then measured as per the procedure of Example 1 to determine bromide ion concentration versus Rel mv. Table 3 below shows the results.

TABLE 3

| ppm of Bromide | Filtrate of Mud G-490 |
| --- | --- |
| 10,000 | −95.2 |
| 8,000 | −90.1 |
| 4,000 | −74.0 |
| 2,000 | −66.7 |
| 1,000 | −56.7 |
| 800 | −58.7 |
| 400 | −54.7 |
| 100 | −50.9 |
| 50 | −18.4 |

When plotted on semilog graph paper, a smooth calibration curve is obtained using the data in Table 3.

EXAMPLE 3

To further demonstrate that the method of the present invention can be used both on the "whole" mud and the mud filtrate, measurements were made on Mud G-524 and its filtrate, Mud G-490 and its filtrate and a third mud, Mud G-619 and its filtrate. In all cases, the bromide ion concentration in the filtrate was 500 ppm by weight. The results are shown in Table 4 below.

TABLE 4

| COMPARISON OF RELATIVE MILLIVOLTS FOR Br⁻ IN MUDS AND FILTRATES | | | |
| --- | --- | --- | --- |
| Mud No. | Rel mv from Mud | Rel mv from Mud Filtrate | Cl⁻ % in Mud |
| 619 | −73.1 | −74.6 | 0.14 |
| 524 | −57.8 | −61.7 | 0.13 |
| 490 | −91.2 | −99.1 | 16.40 |

As can be seen, the relative millivolts between Mud G-619 and its filtrate and Mud G-524 and its filtrate are within 4 mv, but 8 mv for Mud G-490 and its filtrate. As can also be seen from Table 4, the chloride ion content in Mud G-490 is very high indicating that at high chloride levels, interference from chloride must be taken into account in conducting the measurements.

As can be seen from the data above, bromide ion concentration variation in well bore fluids, e.g. drilling muds, can be detected potentiometrically by establishing a calibration curve of bromide ion versus relative millivolts for the mud. If the calibration curve is linear (Example 1), linear regression can be used to obtain a calibration equation. If not, the curve can be treated linear in some region and calibration equations can still be obtained by linear regression (Example 2). If interfering ions are not present, the bromide electrode readings directly from whole mud is about the same as that from mud filtrate. However, as seen from Example 4, when chloride interference is strong, the difference in readings between the whole mud and its filtrate are considerably greater.

EXAMPLE 4

A calibration curve on a drilling mud is prepared as per the procedure of Example 1. A known amount of bromide ion is then added to the drilling mud which is used in the conventional downhole drilling operation. Periodically, samples of the drilling mud returned from downhole are analyzed by the procedure of Example 1 and the results obtained compared with the calibration curve established. From the comparison, the concentration of bromide ion in the used drilling mud samples is determined, and it is determined whether there has been any dilution of the drilling mud from connate water or from surface invasion.

The foregoing disclosure and description of the invention is illustrative and explanatory thereof, and various changes in the method steps may be made within the scope of the appended claims without departing from the spirit of the invention.

What is claimed is:

1. A method of determining the dilution of a wellbore fluid by connate water or surface water invasion comprising preparing a wellbore fluid having a known concentration of bromide ion uniformly distributed in such wellbore fluid, using said wellbore fluid in an earth borehole, recovering a sample of said used wellbore fluid, determining quantitatively the concentration of said bromide ion in said recovered sample, comparing the concentration of bromide ion in said recovered sample with said known concentration of said bromide ion in said wellbore fluid, and determining the dilution of said wellbore fluid.

2. The method of claim 1 wherein the concentration of said bromide ion is determined electrochemically using a bromide ion selective electrode.

3. The method of claim 1 wherein said known concentration of said bromide ion in said well bore fluid is from about 20 parts per million to about 10,000 parts per million.

4. The method of claim 1 wherein said well bore fluid comprises a drilling mud.

* * * * *